United States Patent
Hodges et al.

(10) Patent No.: US 10,568,710 B2
(45) Date of Patent: Feb. 25, 2020

(54) SPINAL PROCEDURE PATIENT DRAPE

(71) Applicant: Variamed, LLC, Chattanooga, TN (US)

(72) Inventors: Scott D. Hodges, Oultewah, TN (US); Christopher B. Young, Chattanooga, TN (US)

(73) Assignee: Variamed, LLC, Chattanooga, TN (US)

( * ) Notice: Subject to any disclaimer, the term of this patent is extended or adjusted under 35 U.S.C. 154(b) by 1572 days.

(21) Appl. No.: 13/741,053

(22) Filed: Jan. 14, 2013

(65) Prior Publication Data

US 2014/0026895 A1    Jan. 30, 2014

Related U.S. Application Data

(60) Provisional application No. 61/586,473, filed on Jan. 13, 2012.

(51) Int. Cl.
   *A61B 46/00*    (2016.01)

(52) U.S. Cl.
   CPC .................. *A61B 46/00* (2016.02)

(58) Field of Classification Search
   CPC ... A61B 19/08; A61B 2019/084; A61B 46/20; A61B 46/00; A61B 46/27
   USPC ................................. 128/849–855
   See application file for complete search history.

(56) References Cited

U.S. PATENT DOCUMENTS

| | | | |
|---|---|---|---|
| 3,383,709 A * | 5/1968 | Bauer | A42B 1/043 2/195.7 |
| 3,750,664 A | 8/1973 | Collins | |
| 3,871,369 A | 3/1975 | Krzewinski | |
| 4,214,320 A * | 7/1980 | Belkin | A41D 13/1209 2/114 |
| 4,384,573 A * | 5/1983 | Elliott | A61B 46/00 128/853 |
| 4,412,532 A * | 11/1983 | Anthony | 600/206 |
| 4,974,604 A * | 12/1990 | Morris | A61B 19/08 128/853 |
| 5,109,873 A | 5/1992 | Marshall | |
| 5,392,917 A * | 2/1995 | Alpern | B65D 77/2056 206/370 |

(Continued)

FOREIGN PATENT DOCUMENTS

WO    WO 93/03933    *    3/1993

*Primary Examiner* — Anna K Kinsaul
*Assistant Examiner* — Camtu T Nguyen
(74) *Attorney, Agent, or Firm* — Davis & Bujold PLLC; Charles W. Fallow

(57) ABSTRACT

A surgical drape is made from a pair of rectangular panels of drape material which are interconnected at a separation zone so that the panels to be pulled apart following a procedure. A fenestration is punched out of the material of one of the panels, near the perforated zone. The fenestration is covered by a flexible, transparent plastic window, preferably made of a polyethylene film and the perimeter of the window is bonded to the drape panel around the fenestration. The window is larger than the fenestration, and is folded or gusseted at its corners so that its center can rise well above the plane of the fenestration, in order to provide clearance for instruments which may be protruding from a surgical site over which the drape is placed.

10 Claims, 1 Drawing Sheet

(56) References Cited

U.S. PATENT DOCUMENTS

| | | | | |
|---|---|---|---|---|
| 5,592,952 | A * | 1/1997 | Bohn | A61B 46/00 128/849 |
| 5,640,975 | A * | 6/1997 | Diao | A61B 46/00 128/849 |
| 5,871,015 | A | 2/1999 | Lofgren et al. | |
| 5,874,372 | A * | 2/1999 | Morishita et al. | 442/182 |
| 6,019,102 | A | 2/2000 | Becker | |
| 6,213,124 | B1 * | 4/2001 | Butterworth | A61B 46/00 128/853 |
| 6,382,212 | B1 | 5/2002 | Borchard | |
| 6,497,233 | B1 | 12/2002 | DeAngelis | |
| 6,647,985 | B1 * | 11/2003 | Prywes | 128/853 |
| 6,675,805 | B1 * | 1/2004 | Graether | 128/849 |
| 6,823,805 | B2 | 11/2004 | Becker | |
| 6,863,071 | B2 * | 3/2005 | Annett et al. | 128/849 |
| 7,104,201 | B2 | 9/2006 | Comeaux et al. | |
| 8,011,371 | B2 * | 9/2011 | Rotolo | A61B 46/00 128/849 |
| 2003/0056698 | A1 | 3/2003 | Comeaux | |
| 2003/0233964 | A1 | 12/2003 | Comeaux | |
| 2005/0072434 | A1 | 4/2005 | Becker | |
| 2008/0283064 | A1 * | 11/2008 | Block | A61B 46/00 128/853 |
| 2011/0297164 | A1 † | 12/2011 | Strauch | |

\* cited by examiner
† cited by third party

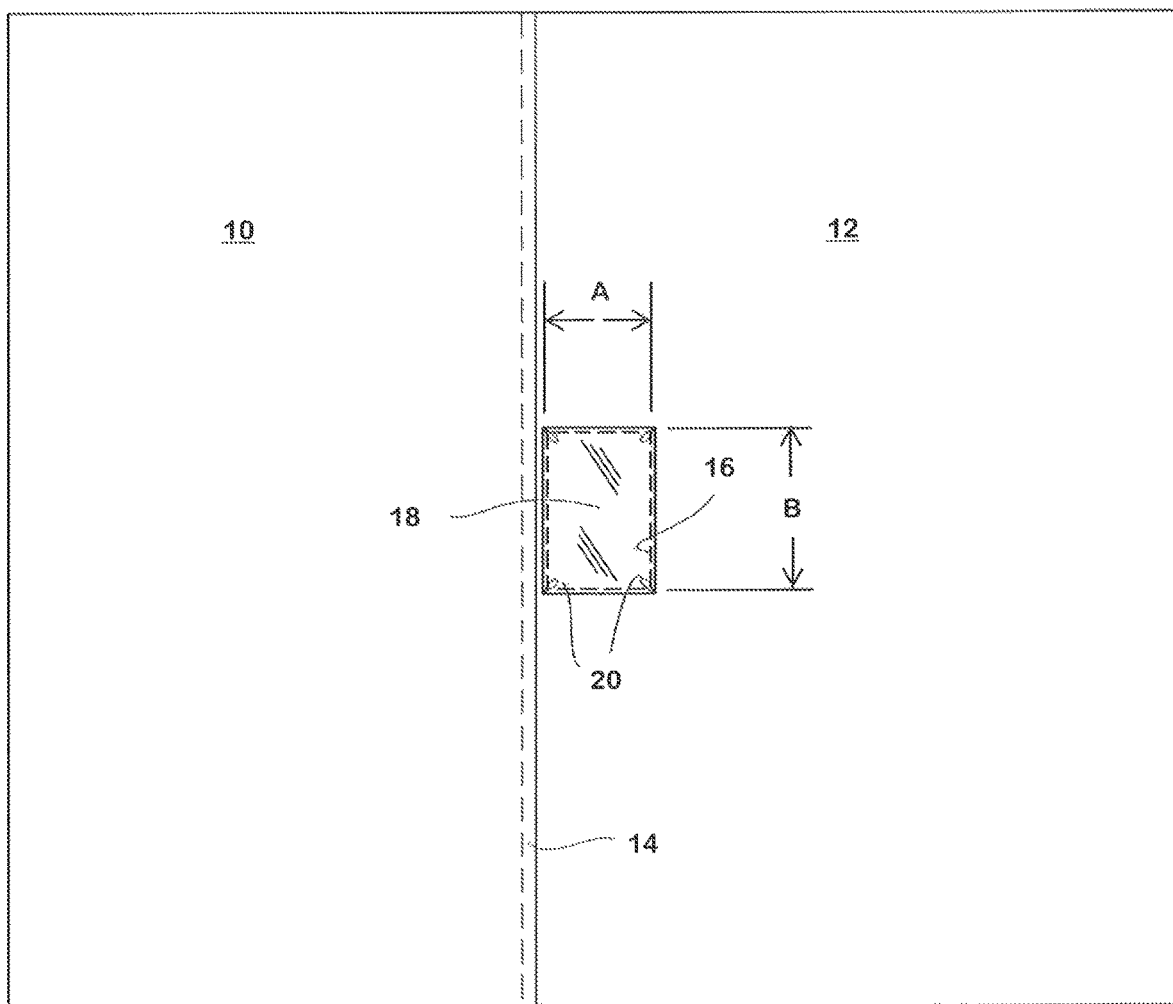

SPINAL PROCEDURE PATIENT DRAPE

This application claims benefit of provisional patent application 61/586,473, filed Jan. 13, 2012.

BACKGROUND OF THE INVENTION

This invention relates to a sterile patient drape for surgical operations, especially spinal procedures.

During surgery, a "sterile field" is defined around the patient. The sterile field does not extend to the floor, but begins a specified distance above the floor. Anything outside or below the sterile field is considered unsterile and may not be brought into or through the sterile field. If a patient drape has a portion which hangs below the sterile field, the drape cannot removed by lifting it without contaminating the sterile field. Conventional drapes are difficult to remove without lifting at least a portion of the drape.

A drape which can be removed without lifting reduces the opportunity for sterile field contamination and the risks, costs and delays which ensue.

During spinal operations, it is sometimes necessary to do imaging of the surgical site after an incision has been made, perhaps with some instrument(s) protruding from the incision. A patient drape having a transparent window with vertical expansibility to accommodate such instrument(s) would prevent contamination of the site, while providing a clear view of the site during the imaging procedure.

SUMMARY OF THE INVENTION

An object of the invention is to provide a simple and inexpensive yet versatile surgical drape that minimizes the potential for sterility breach, by providing a tear-away design.

Another object is to provide a drape which can be placed over a patient during spinal surgery during a medical imaging procedure, to provide a clear view of the surgical site, and to provide clearance for instruments which may be protruding from the surgical site.

These and other objects are attained by a surgical drape at shown in the accompanying drawings and described below.

BRIEF DESCRIPTION OF THE DRAWINGS

In the accompanying drawings,

FIG. 1 is a top plan view of a surgical drape embodying the invention

DESCRIPTION OF THE PREFERRED EMBODIMENT

A surgical drape embodying the invention, as shown in FIG. 1, comprises a pair of preferably rectangular panels 10, 12 of drape material which are interconnected at a separation zone 14, preferably by adhesive tape or by gluing. The glue or adhesive is selected so as to allow the panels to be pulled apart following a procedure. Alternatively, the panels could be formed from a single piece of drape material, and the separation zone could be a line of perforations along which the panels could be torn apart.

In the preferred form of the invention, a window or fenestration 16 is punched out of the material of one of the panels, near the separation zone 14.

While the size of the drape and of the fenestration is not critical and may be varied, for purposes of illustration, the presently preferred drape, shown in FIG. 1, has a size of about 72"×84" (1829 mm×2134 mm); its fenestration has dimensions A,B of about 8"×12" (203 mm×305 mm).

The fenestration 16 is covered by a flexible, transparent plastic window 18, preferably made of a polyethylene film. The perimeter of the window, which is substantially larger than the fenestration, is bonded to the drape panel 12 around the fenestration.

The window is folded to form gussets 20 at its corners, so that the center of the window can rise well above the plane of the fenestration, in order to provide clearance for instruments which may be in place, protruding from the surgical site. The window's gusseted construction enables it to expand vertically about four inches (103 mm), which is sufficient to clear most surgical instruments which might be placed in a spinal site. The expansion height of the window may be varied if desired, as long as substantial room exists for anticipated instrumentation. At a minimum, the expanded height should be at least 20% of the maximum dimension of the fenestration.

In use, the drape is placed over the patient and is aligned so that the surgical site is visible through the fenestration. An imaging procedure such as a CAT scan can then be performed, with the drape protecting the site from contamination. Because the window can expand vertically, the drape can lie flat against the patient, even is an instrument is protruding from the site.

Following the imaging procedure, the drape may be removed by pulling the two panels apart at the separation zone (i.e., along the glue, tape or perforation line) and removing the pieces laterally, from either side of the patient. This avoids having to pull the drape over the patient, so the drape can be kept the prescribed minimum distance from the floor as it is removed.

Since the invention is subject to modifications and variations, it is intended that the foregoing description and the accompanying drawings shall be interpreted as only illustrative of the invention defined by the claims below.

We claim:

1. A drape for protecting an open site of a patient from contamination during a surgical operation while providing visibility of instrumentation which has been placed on the patient at the open site, said drape comprising
   a first fabric panel (10),
   a second fabric panel (12) joined to the first fabric panel along a separation zone,
   a fenestration (18) formed in at least one of the fabric panels (12) for providing visual access to said open site, and
   a transparent window bonded to said at least one of the fabric panels (12) around said fenestration,
   said transparent window being substantially expansible, out of plane in which the fenestration lies, to provide clearance for said instrumentation present at the open site,
   wherein gussets (20) are formed at the corners of the transparent window to enhance its expansibility.

2. The invention of claim 1, wherein the fabric panels are joined at the separation zone by adhesive tape.

3. The invention of claim 1, wherein the transparent window is substantially larger in area than said fenestration.

4. The invention of claim 1, wherein the transparent window is made of a polyethylene film.

5. The invention of claim 1, wherein the fenestration has dimensions (A, B) and a maximum dimension of said dimensions, and the transparent window can expand to a height at least 20% as large as said maximum dimension.

6. The invention of claim 1, wherein the fabric panels are joined at the separation zone by glue.

7. A drape for protecting an open site of a patient during a surgical operation while providing visibility of instrumentation which has been placed at the open site, said drape comprising
- a first fabric panel,
- a second fabric panel joined to the first fabric panel along a separation zone,
- a fenestration formed in one of the fabric panels for providing visual access to said open site, and
- a transparent window bonded to one of the fabric panels around said fenestration,
- said transparent window being substantially expansible, out of plane in which the fenestration lies, to provide clearance for the instrumentation present at the open site.

8. A drape for protecting an open site of a patient from contamination during a surgical operation while providing visibility of instrumentation which has been placed on the patient at the open site, said drape comprising:
- a first fabric panel (10),
- a second fabric panel (12) joined to the first fabric panel along a separation zone,
- a fenestration (18) forced in the second fabric panel (12) for providing visual access to said open site, and
- a transparent window bonded to the second fabric panel (12) around said fenestration,
- one edge of the fenestration being adjacent the separation zone,
- said transparent window being larger in size than a size of the fenestration so as to be able to expand out of plane in which the fenestration lies, to accommodate said instrumentation present at the open site when the drape is placed over the open site and the instrumentation during imaging of the open site, and
- the transparent window being folded, in each of the corners thereof, to form gussets (20) which enhance expansion of the transparent window out of the plane to accommodate the instrumentation, when the drape is placed over the instrumentation during the surgical operation, and facilitate imaging of the open site while preventing contamination of the open site.

9. The drape for protecting an open site of claim 8, wherein the transparent window is made from a polyethylene film, and a perimeter of the polyethylene film is bonded to the second fabric panel around the fenestration.

10. The drape for protecting an open site of claim 8, wherein the gussets facilitate a central region of the window rising by about four inches above the plane of the fenestration in order to accommodate the instrumentation located at the open site.

* * * * *